United States Patent [19]

Travers et al.

[11] Patent Number: 4,727,217

[45] Date of Patent: Feb. 23, 1988

[54] CATALYST FOR ISOMERIZING CUTS OF HIGH NORMAL PARAFFINS CONTENT

[75] Inventors: Christine Travers; Pierre Dufresne; Francis Raatz, all of Rueil-Malmaison; Christian Marcilly, Houilles, all of France

[73] Assignee: Institut Francais du Petrole, Rueil-Malmaison, France

[21] Appl. No.: 1,151

[22] Filed: Jan. 7, 1987

Related U.S. Application Data

[62] Division of Ser. No. 848,547, Apr. 7, 1986, abandoned.

[30] Foreign Application Priority Data

Apr. 7, 1985 [FR] France ................ 85 05351

[51] Int. Cl.$^4$ ................ C07C 5/13
[52] U.S. Cl. ................ 585/739; 585/750; 585/751
[58] Field of Search ............ 585/739, 750, 751

[56] References Cited

U.S. PATENT DOCUMENTS

| | | | |
|---|---|---|---|
| 3,836,597 | 9/1974 | Sie | 585/739 |
| 4,232,181 | 11/1980 | Kiovsky et al. | 585/739 |
| 4,400,576 | 8/1983 | den Otter | 585/739 |

*Primary Examiner*—Curtis R. Davis
*Attorney, Agent, or Firm*—Millen & White

[57] ABSTRACT

The invention concerns a new mordenite adsorbing molecules of a kinetic diameter higher than about 0.66 nm, prepared from a mordenite of the so-called small pores type.

Said zeolite, admixed with a matrix and at least one group VIII metal can be used in n-paraffins hydroisomerization reactions.

7 Claims, No Drawings

CATALYST FOR ISOMERIZING CUTS OF HIGH NORMAL PARAFFINS CONTENT

This is a division of application Ser. No. 848,547 filed Apr. 7, 1986, now abandoned.

The present invention concerns a new catalyst particularly useful for hydroisomerizing a cut containing a large proportion of n-paraffins having 4, 5, 6 or 7 carbon atoms per molecule. The catalyst contains at least one zeolite prepared from a small pores mordenite.

For isomerizing operations, the catalyst conveniently contains, in addition to the zeolite, a matrix and at least one metal pertaining to group VIII of the periodic classification of elements, more particularly platinum, palladium and nickel.

BACKGROUND OF THE INVENTION

The isomerization of normal paraffins of low molecular weight is of high interest in the oil industry, in view of the particularly high octane number of the isoparaffins.

The n-$C_4$ to $C_7$ and mainly $C_5$-$C_6$ paraffins can be advantageously converted to isoparaffins in order to obtain a motor-fuel of high octane number. By this process, the light gasoline fractions, in particular the straight-run top fractions, can be improved.

Three different types of isomerization processes exist:
the low temperature processes (operating at about 20°-130° C.) using a catalyst of the Friedel and Crafts type, such s aluminum chloride,
the "mean" temperature processes (operating at about 150° C.) using as catalyst a supported metal such as platinum on halogenated alumina,
the high temperature processes (operating at 250° C. or more), using zeolite carriers associated with a hydrogenating metal from group VIII.

The thermodynamic equilibrium is more favorable to isoparaffins at low temperature but the catalysts of the Friedel and Crafts type with halogenated alumina carrier, in view of their corrosive nature, require the use of reactors made of very costly special alloys.

The "high temperature" processes are the object, since about 20 years, of many patents. Most of the catalysts disclosed in these patents consist of zeolite, more particularly mordenite, in acid form, with or without hydrogenation promoters. SHELL Company was particulary interested in this process and has claimed catalysts of mordenite base, more particularly:
The mode of exchange of $Na^+$ ions with $NH_4^+$ or $H^{3O}$ ions (U.S. Pat. No. 3,190,939)

| | |
|---|---|
| the acid treatment | succession of hot acid, $NH_4^+$ (USP 3,442,794) |
| | succession of hot acid-cold acid (USP 3,475,345) |
| | acid solution containing $Na^+$ or $K^+$ ions (USP 2,272,737 - USP 4,359,409 - USP 4,400,576) | the thermal treatments with controlled moistness (U.S. Pat. No. 3,836,597—U.S. Pat. No. 3,842,114—U.S. Pat. No. 2,181,928).

ESSO Company, on the other hand, has claimed the following mordenite dealumination processes:
severe acid treatments: HCl 12N, 100° C. (U.S. Pat. No. 3,480,539)
self steaming (roasting in confined atmosphere) between 430° C. and 820° C., followed with acid etching (U.S. Pat. No. 3,506,400).

The self steaming-acid etching succession for dealuminating zeolite is also found in U.S. Pat. No. 3,551,353 to MOBIL.

Two modes of metal deposition are considered:
depositon of metal on the modified zeolite, as in most of the above-mentioned patents.
deposition of the one or more metals on an inert binder, for example alumina, and physical admixture with zeolite in protonic form (U.S. Pat. No. 3,432,568 to MOBIL, U.S. Pat. No. 3,632,835 to UOP, U.S. Pat. No. 4,374,296 to MOBIL).

Particular zeolite treatments, such as fluor introduction, have also been patented (U.S. Pat. No. 3,932,554 to NIPPON oil, U.S. Pat. No. 3,413,370 to UOP).

Mordenite is characterized by a Si/Al atomic ratio ranging generally from 4 to 6: its crystalline structure is formed of $SiO_4$ and $AlO_4$ basic tetrahedron chains, generating two types of channels: channels of dodecagonal opening (contour with 12 oxygens) and channels with octagonal opening (contour with 8 oxygens).

Two types of mordenite exist which differ from each other by their adsorption properties: the variety with wide pores, always synthetic, adsorbs such molecules as benzene (kinetic diameter=0.66 nm (0.66 nanometers) and the variety with small pores, natural or synthetic, which only adsorbs molecules of a kinetic diameter lower than about 0.44 nm. These mordenites also differ by morphological differences-needles for mordenite of small pores, spherulites for mordenite of wide pores—and by structural differences: presence or absence of defects. In the above-mentioned literature, the mordenite used is that of the wide pores type.

Now, the present invention has for object to use a mordenite of the wide pores type prepared from a mordenite of small pores in such operating conditions that the mordenite with wide pores, as used, will have kept the morphology of the mordenite with small pores while nevertheless having the capacity to adsorb the benzene molecule (kinetic diameter: 0.66 nm) at the difference of a mordenite with small pores, as abovementioned. The use of said mordenite of particular morphology (needles), specially treated, gives a substantial increase in activity and selectivity for the isomerization reaction.

It is possible to "unclog" the channels of said particular zeolite by treatment with a strong inorganic acid and/or by roasting in the presence of steam and to obtain an adsorption capacity close to that of the mordenite of wide pores type.

These small pores synthetic mordenites may be obtained by synthesis, particularly in the following conditions: temperature from about 200° to 300° C. and crystallization time from 5 to 50 hours.

SUMMARY OF THE INVENTION

The zeolite used in the catalyst of the present invention is manufactured from a small pores mordenite whose sodium content generally ranges from 4 to 6.5% (by weight) with respect to the weight of dry mordenite. whose Si/Al atomic ratio generally ranges from 4.5 to 6.5 and of mesh volume generally from 2.80 to 2.77 $nm^3$. This mordenite only adsorbs molecules of a kinetic diameter lower than about 0.44 nm. After treatments, the mordenite is characterized by different specifications whose methods of determination will be precisely defined hereinafter: a Si/Al atomic ratio from 5 to 50, preferably from 5 to 30, a sodium content lower than 0.2% by weight, preferably lower than 0.1% by weight with respect to dry zeolite, a mesh volume V, of elementary mesh ranging from 2.78 to 2.73 nm³ and preferably from 2.77 to 2.74 nm³, a benzene adsorption capacity higher than 5%, preferably than 5% with respect to the weight of dry solid (zeolite), a particular morphology, i.e. with a major part as needles, preferably of an average length of 5 microns, whose hexagonal faces have a length of about 1 micron and a "height" of about 0.3 micron.

The different zeolite characteristics are measured by the following methods:

the total Si/Al atomic ratios are determined by X fluorescence, the sodium contents by atomic absorption.

the mesh volume and the crystallinity are determined by X diffraction, the sample being prepared in a similar manner as in the operating mode of Standard ASTM D 3942 80 established for faujasite.

the benzene adsorption capacity of the zeolite is determined by gravimetry. The sample is previously desorbed at 300° C. under $10^{-4}$ Torr ($133.32 \times 10^{-4}$ Pa).

The adsorption is then conducted at 30°C. for 4 hours under a pressure P of 28 Torr (3733 Pa) of benzene, which corresponds to a P/Ps ratio of 0.25, Ps being the saturating vapor pressure at the temperature of the experiment. The adsorbed volumes are calculated from the density of the adsorbate in liquid form at the adsorption temperature: d=0.868.

The so-prepared mordenite, destined to be used in hydroisomerization reactions, is then admixed with a generally amorphous matrix, the hydroisomerization catalyst also containing preferably at least one metal from group VIII, preferably platinum, palladium or nickel. When platinum and palladium are concerned, their content (by weight) ranges from 0.05 to 1%, preferably from 0.1 to 0.6%. For nickel, its weight content is generally from 0.10 to 10% and preferably from 0.2 to 5%. This catalyst constitutes a new hydroisomerization catalyst for cuts containing a large proportion of normal paraffins of 4-7 carbon atoms, preferably 5 or 6 carbon atoms per molecule, whose selectivity and activity are enhanced with respect to the conventional hydroisomerization catalysts.

Various methods are available for obtaining a zeolite or the wide pores type, such as above-defined, from a mordenite of the small pores type. According to a preferred method, the mordenite with small pores is subjected to the different following treatments: sodium cations are exchanged with ammonium cations by dipping the zeolite into a solution of ionizable ammonium salt at a morality generally higher than 0.5, at a temperature generally ranging from 20° to 150° C. This exchange may be repeated several times. The product thus obtained after these cationic exchanges may be washed and then subjected to a thermal treatment in the presence of steam, optionally conducted in accordance with the self steaming technique (roasting in confined atmosphere). The operation is conducted at a temperature from 300° to 800° C., preferably 400°-700° C. for a time of generally more than 10 minutes, preferably more than 20 minutes. The roasting atmosphere contains at least 1%, preferably at least 5% of steam. For self steaming the atmosphere consists essentially of water and ammonia. The so-obtained product may be subjected to acid treatment in view to extract aluminum from the solid. This treatment may be perforby dipping the product into an inorganic or stron organic acid of normality ranging from 0.1 to 12N, at a temperature from 20° to 150° C., preferably from 80° to 150° C., for a time preferably longer than 10 minutes.

The product, after said acid treatment, may be washed, for example with acid, washed with water and then optionally admixed with any convenient matrix. It is then shaped and optionally charged, for example with paltinum and/or palladium and/or nickel, as indicated hereinafter, either before or after the introduction of the matrix, or on the matrix itself. According to another method for preparing the zeolite of the invention, it is also possible to obtain a good catalyst by a different procedure. The small pores mordenite of sodic form may be directly treated in one or more times with an inorganic or organic acid of normality from 0.1 to 12N, at a temperature from 20° to 150° C., preferably 80°-150° C. Here, the alumina amount extracted by this acid treatment must be at least 20% i.e., the Si/Al ratio must be at least about 6.5. It is optionally possible to subsequently complete the sodium cation exchange by treating the product with solution of ionizable ammonium salt. The metal introduction is then performed according to one of the above described procedures.

Other dealumination methods can be considered, such as the etching by hydrofluoric acid, hydrochloric acid in gas phase, or the treatment with fluorosilicate or any other method known in the art.

The modified zeolite, when destined to be used in hydroisomerization reactions, is intimately admixed with a matrix, for example a wet powder of alumina gel. The mixture is then shaped, for example by extrusion through a drawing plate. The mordenite content of the so-obtained carrier must be higher than 40% an preferably higher than 60% (by weight). The shaping may be achieved with other matrices than alumina, such as silica-alumina, natural clays (kaolin or bentonite), alumina-boron oxide . . . and with another technique than extrusion, such as pelletizing, bowl-granulation or any other technique known in the art.

The hydrogenating metal is then deposited on said carrier. Any metal from group VIII may be convenient, in particular platinum, palladium and nickel.

Platinum may be introduced in different ways:

as tetrammine complex by cationic exchange: the metal will then be deposited preferentially on mordenite, as hexachloroplatinic acid: by anionic exchange, the metal will be then preferentially deposited on alumina when alumina is the binder used during the shaping operation.

The first method may be applied for depositing the metal either on the zeolite powder or on a product already shaped, with or without ammonium competitive cation. The metal may also be deposited on extrudates or on powder by the so-called dry impregnation technique. The dried product is then roasted at a temperature from 300° C. to 600° C.

According to the invention, the charge containing a high proportion of light paraffins of 5 or 6 carbon atoms and hydrogen is contacted with a catalyst of the above-described type under isomerizing conditions. This contact may be performed by using the catalyst as fixed bed, fluid bed or batchwise (i.e. discontinuously).

The process is operated between 200° and 300° C., preferably between 230° and 280° C., at $H_2$ partial pressures ranging from atmospheric pressure to 70 bars, preferably from 5 to 50 bars. The space velocity may be from 0.5 to 10 liters of liquid hydrocarbons per liter of catalyst and per hour, preferably from 1 to 5. The H$_2$/change molar ratio may vary within wide limits and is normally ranging from 0.5 to 10, preferably from 1 to 3. The isomerization being a balanced reaction, the isomerizate still contains a substantial amount of unconverted n-paraffins. These paraffins may be separated from the isomers, for example by distillation or fractionation over molecular sieve, and recycled into the isomerization unit.

EXAMPLES

The following examples illustrate the invention without however limiting the scope thereof.

The performances are expressed in term of n-hexane conversion and of isomerization selectivity, defined as follows:

$$\text{Conversion} = \frac{\text{n-hexane weight input} - \text{n-hexane weight output} \times 100}{\text{n-hexane weight input}}$$

$$\text{Selectivity} = \frac{\Sigma(\text{isomers weight}) \times 100}{\Sigma(\text{weight of the reaction products})}$$

EXAMPLE 1

Preparation of catalyst A according to the invention.

The raw material is a mordenite with small pores, referenced Alite 150, manufactured by Société Chimique de la Grande Paroisse. Its chemical formula in anhydrous state is: NaAlO$_2$(SiO$_2$)$_{5.5}$ and its benzene adsorption capacity is 1% by weight with respect to the weight of dry solid (mesh volume: 2.79 nm$^3$; sodium content: 5.3% by weight, kinetic diameter of adsorbed molecules: 0.38 nm); 50 g of said powder are dipped into a 2M ammonium nitrate solution and the suspension is brought to 95° C. for 2 hours.

The volume of involved ammonium nitrate solution is four times the weight of dry zeolite (V/P=4). This cationic exchange operation is renewed three times. After the third exchange, the product is washed with water at 20° C. for 20 minutes, with a V/P ratio equal to 4. The sodium content, expressed in percent by weight with respect to the dry weight, decreases from 5.5 to 0.1%. The product is then filtered and subjected to roasting in confined atmosphere (self steaming) at 600° C. for 2 hours.

Then an acid etching is performed with 0.58N hydrochloric acid, by supplying the product at reflux to the hydrochloric acid aqueous solution at 90° C. for 2 hours with a V/P ratio equal to 8. The product is then filtered, washed with 0.1N hydrochloric acid, then with water.

The Si/Al atomic ratio of said mordenite is equal to 12; its mesh volume is 2.750 nm$^3$, its sodium content 300 ppm and its benzene adsorption capacity 9.6% by weight with respect to the weight of dry solid. The morphology of said mordenite is that of needles having an average length of 5 μm, whose faces are hexagonal and have a length of about 1 μm and a height of about 0.3 μm. The so-modified mordenite is then mixed with a binder of the bentonite type and the resultant mixture, containing 25% by weight of bentonite, is forced through a drawing plate. The extrudates of 1.2 mm diameter are then dried and roasted. 0.4% of platinum are then deposited on said carrier by cationic exchange from tetramine platinum chloride Pt(NH$_3$)$_4$Cl$_2$ with ammonium nitrate as competitive ion. The sodium amount in the final catalyst is 80 ppm. The Si/Al atomic ratio is equal to 12 and the mesh volume to 2.750 nm$^3$. The extrudates are then dried and roasted at 500° C.

The so-obtained catalyst is charged into a catalytic unit as fixed bed and reduced in hydrogen at 450° C. It is then tested with a charge of normal hexane in the following conditions: temperature of 250° C., pressure of 30 bars, n-hexane weight per unit weight of mordenite and per hour: 2, hydrogen to normal hexane molar ratio: 2. The performances reported in table I are those obtained after 30 h of run of the catalyst.

EXAMPLE 2

Preparation of catalyst B according to the invention

Example 2 differs from example 1 in that the mordenite dealumination is no longer obtained by succession of treatments, exchanges, self-steaming, acid etching but only by acid treatment consisting of 3 successive acid etchings with HCl/N at 100° C. for 2 h. The Si/Al atomic ratio is 12, the mesh volume 2.759 nm$^3$, the benzene adsorption capacity 7.9%. This mordenite has a morphology of needles whose sizes are substantially the same as for catalyst A. The subsequent steps of the preparation are similar to those of example 1. The platinum content is 0.4% and the sodium content 90 ppm. The performances summarized in table I are slightly lower than those obtained with catalyst A.

EXAMPLE 3

Preparation of catalyst C, not conforming with the invention

In example 3 the mordenite with small pores, as described in example 1, is just exchanged 4 times in 2M ammonium nitrate solutions, but not subjected to acid or thermal treatments. The Si/Al ratio is equal to 5.5, the sodium content to 300 ppm and the mesh volume to 2.778 nm$^3$, the benzene adsorption capacity being 1.2% by weight. The catalyst is then prepared as in example 1, with a 0.4% platinum content. The performances summarized in table I shown that, as a result of the clogged structure of the small pores mordenite, the isomerization activity is very low.

EXAMPLE 4

Preparation of catalyst D, conforming with the invention

Catalyst D differs from catalyst A described in example 1 in that successive exchanges are performed with 2M ammonium nitrate solutions at 95° C. and followed with self-steaming at 600° C. The Si/Al atomic ratio is then 5.5, the mesh volume 2.755 nm$^3$, the benzene adsorption capacity 7.20%. This catalyst is in form of needles whose sizes are substantially the same as those of catalyst A. The catalyst is then prepared as in example 1. It contains 0.4% of platinum and 90 ppm of sodium. The obtained performances are lower than those obtained with catalyst A according to the invention and are close to those obtained with catalyst B.

EXAMPLE 5

Preparation of catalyst E, not conforming with the invention

Catalyst E differs from catalyst A, described in example 1, in that the mordenite is of the wide pores type, used as powder referenced Zeolon 100 Na, manufactured by NORTON Company.

50 g of said powder are brought to reflux for 2 hours at 950° C. in a sodium nitrate solution. This exchange is renewed 3 times. After the last exchange, the product is washed with water for 20 mn at 20° C., filtered and roasted in confined atmospheere (self-steaming) at 600° C. for 2 hours. This thermal treatment is followed with an acid etching with 0.58N hydrochloric acid. The solid is brought to reflux in an aqueous solution of hydrochloric acid at 90° C. for 2 hours, then washed with water.

The Si/Al atomic ratio of the obtained zeolite is 12, the mesh volume 2.752 nm$^3$ and the sodium content 95 ppm. This product, in contrast with the mordenite according to the invention, has not a needle morphology. The obtained product is then shaped by mixing with an alumina gel, previously peptized.

The mixture containing 25% by weight of alumina is forced through a drawing plate. The extrudates of 1.2 mm are then dried and roasted and 0.4% of platinum are then deposited on this product, according to the technique described in example 1.

The performances reported for isoconditions in table I are 20 points lower than those obtained with catalyst A according to the invention.

EXAMPLE 6

Preparation of catalyst F, not conforming with the invention

Catalyst F differs from catalyst E described in example 5 only in that it has not been subjected to exchanges and thermal treatments but only to three successive acid treatments. The powdery zeolite of wide pores type is brought to reflux at 100° C. for 2 h in N hydrochloric acid. The platinum deposition procedure is identical to that described in the preceding examples. The Si/Al atomic ratio of the obtained zeolite is 12, the volume of elementary mesh 2.751 nm$^3$, the sodium content 100 ppm and the platinum content 0.4%. This zeolite has not a needle configuration.

The performances reported in table I are equivalent to those obtained with catalyst E, but 20 points below those obtained with catalyst A according to the invention.

about 5 to 50, a sodium content lower than 0.2% by weight with respect to the total amount of the dry mordenite, a unit cell volume V of elementary mesh from 2.78 to 2.73 nm$^3$, a benzene adsorption capacity higher than 5% by weight with respect to the weight of the dry mordenite, the mordenite being in major part of needle configuration.

2. A process according to claim 1 wherein the catalyst has a Si/Al atomic ratio from 5.5 to 30, a sodium content lower than 0.1% by weight with respect to the total amount of dry mordenite, a volume of elementary mesh from 2.77 to 2.74 nm$^3$, a benzene adsorption capacity higher than 8% with respect to the weight of dry mordenite, the mordenite being in major part formed as needles whose average length is 5 μm and whose faces, in major part hexagonal, have a length of about 1 μm and a height of about 0.3 μm.

3. A process according to claim 1, wherein the mordenite catalyst further contains a matrix and at least one metal from group VIII of the periodic classification of elements.

4. A process according to claim 3, wherein the metal is selected from the group consisting of platinum, palladium and nickel.

5. A process according to claim 4, wherein the group VIII metal content ranges, in proportion by weight with respect to the total catalyst weight, from 0.05 to 1% when the metal is platinum or palladium and from 0.10 to 10% when the metal is nickel.

6. A process according to claim 1 wherein said catalyst is produced from a small pore mordenite whose sodium content is 4 to 6.5% by weight with respect to the dry mordenite, whose Si/Al atomic ratio is 4.4 to 6.5 and whose unit cell volume is generally from 2.80 to 2.77 nm$^3$, said mordenite adsorbing molecules of kinetic diameter lower than about 0.44 nm, said process being characterized by the steps of:
(a) exchanging one or more times sodium cations of the small pore mordenite with ammonium cations,
(b) treating the product obtained in step (a) at a temperature from 300° to 800° C. in an atmosphere whose water content is at least 1%,

TABLE I

| EXAMPLE | CATALYST | MORDENITE RAW MATERIAL | APPLIED TREATMENT | | | CONVERSION | SELECTIVITY |
| | | | Exchange NH$_4^+$ | Roasting in confined atmosphere | Acid Treatment | | |
| --- | --- | --- | --- | --- | --- | --- | --- |
| 1 | A | Alite 150 | X | X | X | 79.5 | 98.6 |
| 2 | B | Alite 150 | | | X | 70.2 | 97.3 |
| 3 | C | Alite 150 | X | | | 7 | 97 |
| 4 | D | Alite 150 | X | X | | 68 | 97 |
| 5 | E | Zeolon 100 Na | X | X | X | 56.2 | 96.5 |
| 6 | F | Zeolon 100 Na | | | X | 55.5 | 96.5 |

What is claimed as the invention is:

1. In a process comprising hydroisomerizing a cut containing a large proportion of n-paraffins having 4 to 7 carbon atoms per molecule, said hydroisomerizing being conducted in contact with a catalyst, the improvement which comprises employing a catalyst whose basic constituent is a wide pore mordenite capable of adsorbing molecules of a kinetic diameter larger than about 0.66 nm, having a Si/Al atomic ratio from (c) treating a resultant product with an inorganic or orgnic acid of normality ranging from 0.1 to 12N, at a temperature from 20° to 150° C., and
(d) shaping a resultant mass.

7. A process according to claim 6 wherein step (b) of the process of producing the catalyst, the water content of said atmosphere is at least 5%.

* * * * *